(12) United States Patent
Chegini et al.

(10) Patent No.: US 10,660,762 B2
(45) Date of Patent: May 26, 2020

(54) MINIMALLY INVASIVE BIOMATERIAL INJECTION SYSTEM

(71) Applicant: DePuy Synthes Products, Inc., Raynham, MA (US)

(72) Inventors: Salman Chegini, Oberdorf (CH); Joern Richter, Oberdorf (CH); Daniel Thommen, Oberdorf (CH)

(73) Assignee: DePuy Synthes Product, Inc., Raynham, MA (US)

( * ) Notice: Subject to any disclaimer, the term of this patent is extended or adjusted under 35 U.S.C. 154(b) by 431 days.

(21) Appl. No.: 15/401,229

(22) Filed: Jan. 9, 2017

(65) Prior Publication Data

US 2017/0112629 A1   Apr. 27, 2017

Related U.S. Application Data

(63) Continuation of application No. 14/025,448, filed on Sep. 12, 2013, now Pat. No. 9,539,041.

(51) Int. Cl.
*A61B 17/88* (2006.01)
*A61F 2/44* (2006.01)
(Continued)

(52) U.S. Cl.
CPC .......... *A61F 2/441* (2013.01); *A61B 17/7097* (2013.01); *A61B 17/7098* (2013.01);
(Continued)

(58) Field of Classification Search
CPC ........................ A61B 17/8805; A61B 17/8825
See application file for complete search history.

(56) References Cited

U.S. PATENT DOCUMENTS 2,381,050 A   12/1943   Hardinge
3,701,703 A   10/1972   Zimmer et al.
(Continued)

FOREIGN PATENT DOCUMENTS

EP   0493789   7/1992
EP   0872257   10/1998
(Continued)

OTHER PUBLICATIONS

Cotten, M.D., Anne, et al., "Percutaneous Vertebroplasty for Osteolytic Metastases and Myeloma: Effects of the Percentage of Lesion Filling and the Leakage of Methyl Methacrylate at Clinical Follow-up," Radiology, vol. 200, 1996, pp. 525-530.
(Continued)

*Primary Examiner* — Nicholas W Woodall
(74) *Attorney, Agent, or Firm* — Meunier Carlin & Curfman LLC

(57) ABSTRACT

This invention relates generally to an instrumentation and implant system providing minimally invasive vertebral augmentation. The apparatus including an expandable membrane sized and configured to be located within a cavity in a patient's bone and having an interior volume for receiving bone filler material; a delivery cannula in communication with the membrane for providing bone filler material to the membrane; and an evacuation cannula in fluid communication with the membrane for receiving a portion of the provided bone filler material from the membrane.

19 Claims, 10 Drawing Sheets

(51) Int. Cl.
*A61B 17/70* (2006.01)
*A61F 2/46* (2006.01)

(52) U.S. Cl.
CPC ...... *A61B 17/8805* (2013.01); *A61B 17/8811* (2013.01); *A61B 17/8816* (2013.01); *A61B 17/8819* (2013.01); *A61B 17/8825* (2013.01); *A61B 17/8827* (2013.01); *A61F 2/4601* (2013.01); *A61F 2/4611* (2013.01)

(56) References Cited

U.S. PATENT DOCUMENTS

| | | |
|---|---|---|
| 3,867,728 A | 2/1975 | Stubstad et al. |
| 4,055,029 A | 10/1977 | Kalbow et al. |
| 4,311,146 A | 1/1982 | Wonder |
| 4,364,392 A | 12/1982 | Strother et al. |
| 4,735,625 A | 4/1988 | Davidson |
| 4,755,184 A | 7/1988 | Silverberg |
| 4,819,637 A | 4/1989 | Dormandy, Jr. et al. |
| 4,820,349 A | 4/1989 | Saab |
| 4,969,888 A | 11/1990 | Scholten et al. |
| 5,041,114 A | 8/1991 | Chapman et al. |
| 5,049,132 A | 9/1991 | Shaffer et al. |
| 5,059,193 A | 10/1991 | Kuslich |
| 5,098,381 A | 3/1992 | Schneider |
| 5,108,404 A | 4/1992 | Scholten et al. |
| 5,176,692 A | 1/1993 | Wilk et al. |
| 5,192,326 A | 3/1993 | Bao et al. |
| 5,390,683 A | 2/1995 | Pisharodi |
| 5,411,475 A | 5/1995 | Atala et al. |
| 5,443,496 A | 8/1995 | Schwartz et al. |
| 5,514,092 A | 5/1996 | Forman et al. |
| 5,549,679 A | 8/1996 | Kuslich |
| 5,571,189 A | 11/1996 | Kuslich |
| 5,599,301 A | 2/1997 | Jacobs et al. |
| 5,601,593 A | 2/1997 | Freitag |
| 5,674,295 A | 10/1997 | Ray et al. |
| 5,693,100 A | 12/1997 | Pisharodi |
| 5,707,390 A | 1/1998 | Bonutti |
| 5,759,191 A | 6/1998 | Barbere |
| 5,800,392 A | 9/1998 | Racchini |
| 5,827,289 A | 10/1998 | Reiley et al. |
| 5,830,228 A | 11/1998 | Knapp et al. |
| 5,893,850 A | 4/1999 | Cachia |
| 5,972,015 A | 10/1999 | Scribner et al. |
| 5,993,484 A | 11/1999 | Shmulewitz |
| 6,096,038 A | 8/2000 | Michelson |
| 6,127,597 A | 10/2000 | Beyar et al. |
| 6,179,856 B1 | 1/2001 | Barbere |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,293,960 B1 | 9/2001 | Ken |
| 6,306,177 B1 | 10/2001 | Felt et al. |
| 6,395,032 B1 | 5/2002 | Gauchet |
| 6,402,784 B1 | 6/2002 | Wardlaw |
| 6,440,138 B1 | 8/2002 | Reiley et al. |
| 6,478,800 B1 | 11/2002 | Fraser et al. |
| 6,547,804 B2 | 4/2003 | Porter et al. |
| 6,558,390 B2 | 5/2003 | Cragg |
| 6,565,606 B1 | 5/2003 | Bruce et al. |
| 6,613,054 B2 | 9/2003 | Scribner et al. |
| 6,620,162 B2 | 9/2003 | Kuslich et al. |
| 6,632,235 B2 | 10/2003 | Weikel et al. |
| 6,638,246 B1 | 10/2003 | Naimark et al. |
| 6,663,647 B2 | 12/2003 | Reiley et al. |
| 6,679,886 B2 | 1/2004 | Weikel et al. |
| 6,706,069 B2 | 3/2004 | Berger |
| 6,716,216 B1 | 4/2004 | Boucher et al. |
| 6,719,761 B1 | 4/2004 | Reiley et al. |
| 6,726,691 B2 | 4/2004 | Osorio et al. |
| 6,733,532 B1 | 5/2004 | Gauchet et al. |
| 6,736,793 B2 | 5/2004 | Meyer et al. |
| 6,740,093 B2 | 5/2004 | Hochschuler et al. |
| 6,852,095 B1 | 2/2005 | Ray |
| 6,855,153 B2 | 2/2005 | Saadat |
| 6,863,672 B2 | 3/2005 | Reiley et al. |
| 6,899,719 B2 | 5/2005 | Reiley et al. |
| 6,969,404 B2 | 11/2005 | Ferree |
| 6,981,981 B2 | 1/2006 | Reiley et al. |
| 7,001,431 B2 | 2/2006 | Bao et al. |
| 7,011,684 B2 | 3/2006 | Eckman |
| 7,025,771 B2 | 4/2006 | Kuslich et al. |
| 7,044,954 B2 | 5/2006 | Reiley et al. |
| 7,097,648 B1 | 8/2006 | Globerman et al. |
| 7,153,307 B2 | 12/2006 | Scribner et al. |
| 7,166,121 B2 | 1/2007 | Reiley et al. |
| 7,175,627 B2 | 2/2007 | Lin et al. |
| 7,175,628 B2 | 2/2007 | Lin et al. |
| 7,175,629 B2 | 2/2007 | Lin et al. |
| 7,226,481 B2 | 6/2007 | Kuslich |
| 7,226,648 B2 | 6/2007 | Al Ghatta et al. |
| 7,241,303 B2 | 7/2007 | Reiss et al. |
| 7,261,720 B2 | 8/2007 | Stevens et al. |
| 7,655,010 B2 | 2/2010 | Serhan et al. |
| 7,699,894 B2 | 4/2010 | O'Neil |
| 8,043,381 B2 | 10/2011 | Hestad et al. |
| 8,057,528 B2 | 11/2011 | Parker |
| 8,147,517 B2 | 4/2012 | Trieu et al. |
| 8,167,944 B2 | 5/2012 | Kim |
| 8,357,384 B2 | 1/2013 | Behnam et al. |
| 8,403,937 B2* | 3/2013 | Schwardt ............ A61B 17/8811 606/279 |
| 8,518,115 B2 | 8/2013 | Chavatte et al. |
| 9,539,042 B2* | 1/2017 | Paris ................ A61B 17/8822 |
| 2002/0058947 A1 | 5/2002 | Hochschuler et al. |
| 2002/0068974 A1 | 6/2002 | Kuslich et al. |
| 2003/0187473 A1 | 10/2003 | Berenstein et al. |
| 2003/0220649 A1 | 11/2003 | Bao et al. |
| 2003/0220666 A1 | 11/2003 | Mirigian et al. |
| 2004/0054414 A1 | 3/2004 | Trieu et al. |
| 2004/0073308 A1 | 4/2004 | Kuslich et al. |
| 2004/0097930 A1 | 5/2004 | Justis et al. |
| 2004/0098017 A1 | 5/2004 | Saab et al. |
| 2004/0102774 A1 | 5/2004 | Trieu |
| 2004/0143288 A1 | 7/2004 | Searle |
| 2004/0167561 A1 | 8/2004 | Boucher et al. |
| 2004/0167625 A1 | 8/2004 | Beyar et al. |
| 2004/0210297 A1 | 10/2004 | Lin et al. |
| 2004/0215343 A1 | 10/2004 | Hochschuler et al. |
| 2004/0215344 A1 | 10/2004 | Hochschuler et al. |
| 2004/0220615 A1 | 11/2004 | Lin et al. |
| 2005/0010297 A1 | 1/2005 | Watson et al. |
| 2005/0070911 A1 | 3/2005 | Carrison et al. |
| 2005/0143827 A1 | 6/2005 | Globerman et al. |
| 2005/0209595 A1 | 9/2005 | Karmon |
| 2005/0209629 A1 | 9/2005 | Kerr et al. |
| 2005/0234498 A1 | 10/2005 | Gronemeyer et al. |
| 2005/0273049 A1 | 12/2005 | Krulevitch et al. |
| 2006/0009844 A1 | 1/2006 | Bloemer et al. |
| 2006/0079905 A1 | 4/2006 | Beyar et al. |
| 2006/0100706 A1* | 5/2006 | Shadduck .......... A61B 17/1617 623/17.11 |
| 2006/0106459 A1 | 5/2006 | Truckai et al. |
| 2006/0149379 A1 | 7/2006 | Kuslich et al. |
| 2006/0155296 A1 | 7/2006 | Richter |
| 2006/0173464 A1 | 8/2006 | Ellman et al. |
| 2006/0182780 A1 | 8/2006 | Riley et al. |
| 2006/0190083 A1 | 8/2006 | Arnin et al. |
| 2006/0217736 A1 | 9/2006 | Kaneko et al. |
| 2006/0229625 A1 | 10/2006 | Truckai et al. |
| 2006/0235425 A1 | 10/2006 | Lin et al. |
| 2006/0271061 A1 | 11/2006 | Beyar et al. |
| 2006/0293750 A1 | 12/2006 | Sherman et al. |
| 2007/0055266 A1 | 3/2007 | Osorio et al. |
| 2007/0055267 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio et al. |
| 2007/0093899 A1 | 4/2007 | Dutoit et al. |
| 2007/0156251 A1 | 7/2007 | Karmon |
| 2007/0168031 A1 | 7/2007 | Hudgins et al. |
| 2007/0213760 A1 | 9/2007 | Hayes et al. |
| 2007/0219490 A1 | 9/2007 | Pepper et al. |

(56) References Cited

U.S. PATENT DOCUMENTS

| | | |
|---|---|---|
| 2007/0233258 A1 | 10/2007 | Hestad et al. |
| 2007/0282443 A1 | 12/2007 | Globerman et al. |
| 2008/0027546 A1 | 1/2008 | Semler et al. |
| 2008/0086133 A1 | 4/2008 | Kuslich et al. |
| 2008/0108860 A1 | 5/2008 | Bell et al. |
| 2008/0154273 A1 | 6/2008 | Shadduck et al. |
| 2008/0249604 A1 | 10/2008 | Donovan et al. |
| 2009/0069850 A1 | 3/2009 | Fuerderer |
| 2010/0262240 A1 | 10/2010 | Chavatte et al. |
| 2010/0274255 A1 | 10/2010 | Donovan et al. |
| 2011/0218544 A1 | 9/2011 | Mirza |
| 2013/0230454 A1* | 9/2013 | Gardner ............ A61K 38/18 424/1.11 |

FOREIGN PATENT DOCUMENTS

| | | |
|---|---|---|
| WO | 1995/005209 | 2/1995 |
| WO | 1998/056301 | 12/1998 |
| WO | 2001/076514 | 10/2001 |
| WO | 2002/043628 | 6/2002 |
| WO | 2003/007853 | 1/2003 |
| WO | 2005/048856 | 6/2005 |
| WO | 2006/034396 | 3/2006 |
| WO | 2009/084109 | 7/2009 |

OTHER PUBLICATIONS

Cotten, M.D., Anne, et al., "Preoperative Percutaneous Injection of Methyl Methacrylate and N-Butyl Cyanoacrylate in Vertebral Hemangiomas," AJNR, vol. 17, 1996, pp. 137-142.

Gangi, Afshin, et al., "Percutaneous Vertebroplasty Guided by a Combination of CT and Fluoroscopy," AJNR, vol. 15, Jan. 1994, pp. 83-86.

Maciunas, M.D., R.J., "Endovascular Neurological Intervention," American Association of Neurological Surgeons, 1995, pp. 153-158.

Jensen, Mary E., et al., "Percutaneous Polymethylmethacrylate Vertebroplasty in the Treatment of Osteoporotic Vertebral Body Compression Fractures: Technical Aspects," AJNR, vol. 18, No. 10, Nov.-Dec. 1997, pp. 1897-1904.

Saab, Mark A., "Applications of High-Pressure Balloons in the Medical Device Industry," 1999, 19 pages.

International Search Report, dated Nov. 28, 2014, received in connection with International Patent Application No. PCT/US2014/053691.

International Search Report, dated Jun. 15, 2009, received in connection with International Patent Application No. PCT/US2008/083350.

International Preliminary Report on Patentability and Written Opinion, dated May 18, 2010, in International Application No. PCT/US2008/083350.

* cited by examiner

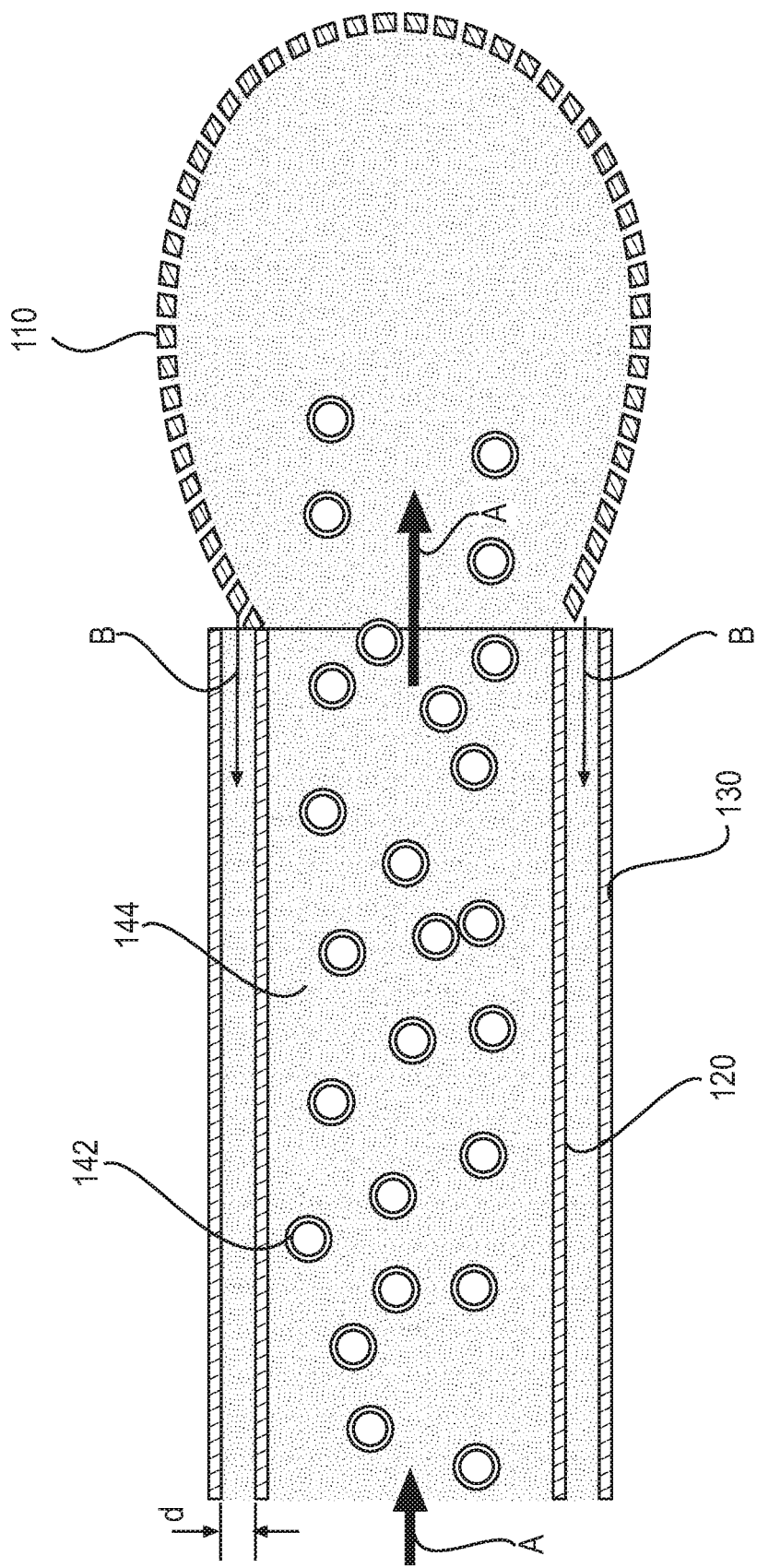

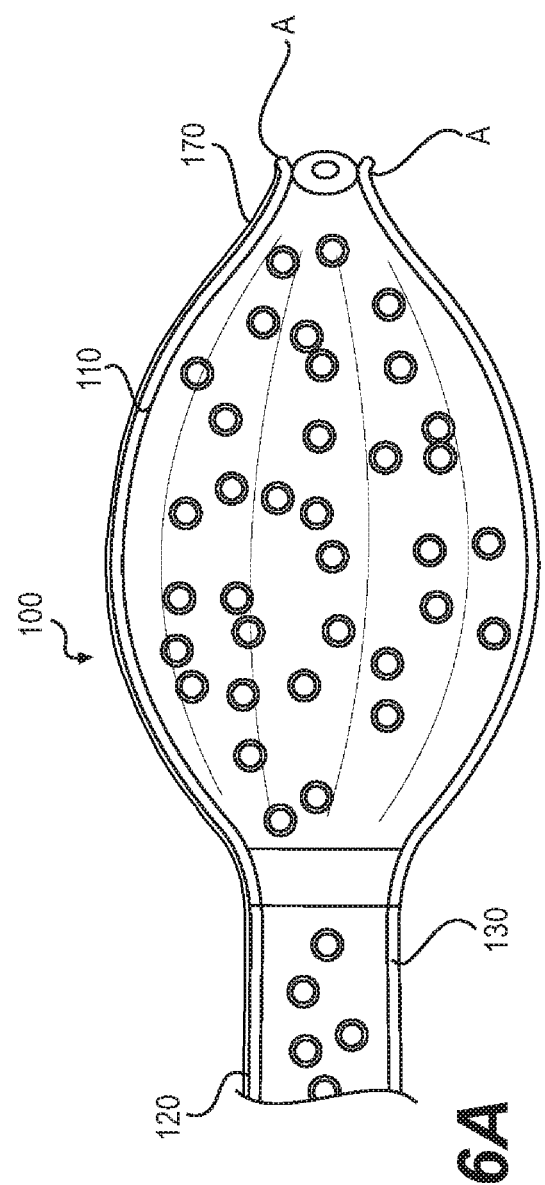
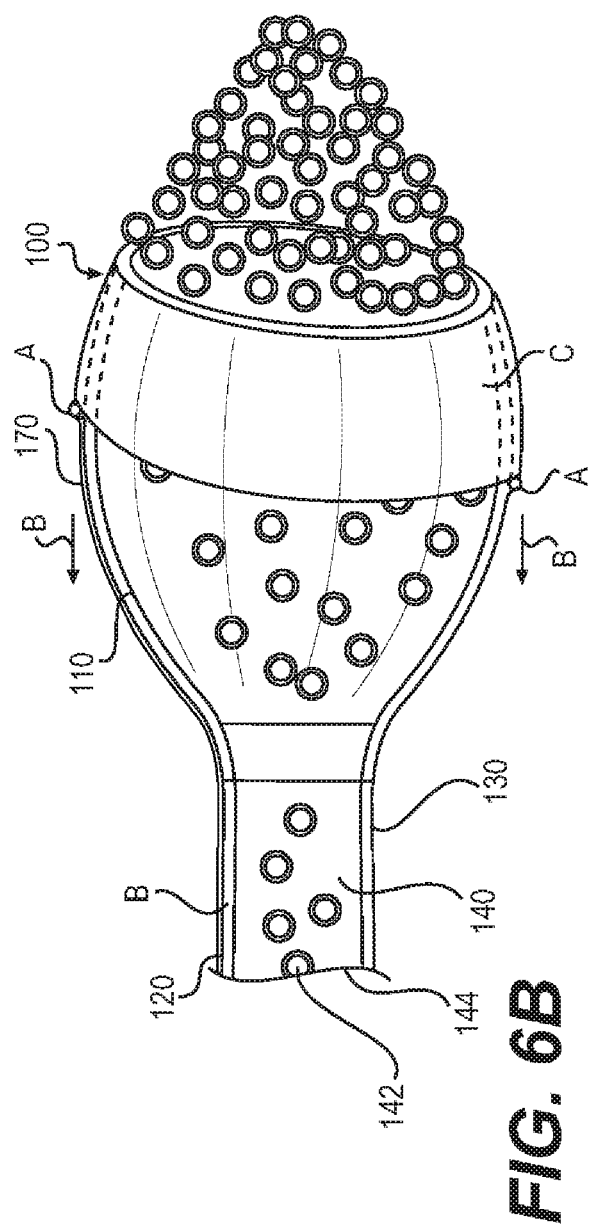
FIG. 6A
FIG. 6B

MINIMALLY INVASIVE BIOMATERIAL INJECTION SYSTEM

CROSS REFERENCE TO RELATED APPLICATIONS

This application is a continuation of U.S. application Ser. No. 14/025,448 (issued as U.S. Pat. No. 9,539,041), filed Sep. 12, 2013, entitled "Minimally Invasive Biomaterial Injection System," the disclosure of which is hereby incorporated by reference.

TECHNICAL FIELD

This invention relates generally to an instrumentation and implant system for augmenting or supporting bones or other structures including, for example, a vertebral body or intervertebral disc space. More specifically, this invention relates to a porous or permeable containment device and associated methods and instrumentation for the treatment of compressed bone voids, more specifically, vertebral compression fractures and intervertebral disc space.

BACKGROUND

There are various pathologies which results in creation a bone the void including vertebral compression fractures, tumors in bony sections (e.g., vertebral bodies), and treatment of disc degeneration where the degenerated disc is removed and replaced with an implant. To fill the gap which is created during surgery/degeneration, insertion of a biomaterial is required for providing a bone growth environment (conductive/inductive) as well as for enhancing the mechanical stability of the bone.

Vertebral compression fractures ("VCF") represent a common spinal injury and may result in prolonged disability. Generally speaking, VCF involves collapse of one or more vertebral bodies in the spine. VCF usually occurs in the lower vertebrae of the thoracic spine or the upper vertebrae of the lumbar spine and generally involves fracture of the anterior portion of the affected vertebral body. Such spinal compression fractures and related spinal deformities, if not successfully treated, can lead to deformation of the normal alignment or curvature, e.g., lordosis, of the affected area of the spine, as well as chronic complications and an overall adverse impact upon the quality of life for the patient. Until recently, doctors were limited to treating such compression fractures and related deformities with pain medications, bed rest, bracing or invasive spinal surgery.

More recently, minimally invasive surgical procedures for treating vertebral compression fractures, tumors in the bony sections (e.g., vertebral bodies), and disc degeneration have been developed. These procedures generally involve the insertion of a rigid cannula, needle or trocar into the interior of a collapsed or otherwise damaged vertebra. The cannula usually includes a lumen or central passage through which another tool, implant or filler material is passed in order to reposition and/or augment the vertebral body.

Delivering originally solid state biomaterial (e.g., autograft bone) through a minimally invasive access (cannula) to fill the created void has proven to be challenging procedure due to the geometrical constraints of the access cannula as well as friction between bone particles within the cannula during insertion. The most basic of these procedures is vertebroplasty. Vertebroplasty involves injecting a medical-grade bone cement (such as polymethylmethacrylate, a.k.a., PMMA) via a special bone needle into a fractured vertebra. The bone cement is injected with sufficient pressure to compress and displace cancellous bone tissue. However, the direction and containment of the injected cement can be difficult to control because the space the bone cement occupies is ill-defined, self-forming, and highly-dependent upon the internal composition of the cancellous bone. Additionally, vertebroplasty does not always reposition the fractured bone and therefore may not address the problem of spinal deformity due to fracture.

A number of more advanced treatments for vertebral compression fractures, tumors in the bony sections, and disc degeneration are known, and generally involve two phases: (1) reposition, or restoration of the original height/shape of the vertebral body/bone void (and consequent lordotic correction of the spinal curvature); and (2) augmentation, or addition of material to support or strengthen the fractured bone. Such procedures generally involve use of a cannula, catheter, needle, trocar or other introducer to provide access to the interior of the effected vertebral body.

Procedures, such as kyphoplasty, provide better bounding and control over injected bone cement, other procedures utilize devices for first forming cavities within the cancellous bone (and, accordingly, other interior body regions) prior to injecting bone cement into such a cavity. During balloon kyphoplasty (Kyphon, Inc.), an expandable body or balloon is deployed into the interior body region to form a cavity in, for example, cancellous bone tissue surrounded by fractured cortical bone. Kyphoplasty then achieves the reconstruction of the lordosis, or normal curvature, by inflating the balloon, which expands within the vertebral body restoring it to its original height. These expandable body devices effectively compress and displace the cancellous bone to form an interior cavity that then receives a filling material intended to provide renewed interior structural support for cortical bone.

A common drawback of most systems for repositioning and augmenting damaged vertebrae/bone voids is that they involve the use of multiple complex instruments introduced through rigid introducers. These introducers limit the surgeon's ability to access portions of the patient's spine. Similarly, these systems do not allow the surgeon to control the location and composition of the bone cerement provided to the bone cavity. Furthermore, delivering bone graft and solid state material into the intervertebral disc space through a minimally invasive access is challenging as the solid state material tends to jam on the way to the intended point. Accordingly, there remains a need in the art to provide a safe and effective apparatus and methods for minimally invasive repositioning of and osteopathic augmentation of vertebral bodies to restore lordosis of the spine.

SUMMARY

Presented are systems and methods for minimally invasive vertebral augmentation and restoration of spinal lordosis. An aspect of the present invention is directed to an apparatus including a porous or permeable membrane is provided into an interior volume/void in a targeted vertebral body. The membrane configured to receive bone filler material thereby restoring the anatomy of the targeted vertebral body. The apparatus including an expandable membrane sized and configured to be located within the cavity in the patient's bone, the expandable membrane having an interior cavity for receiving the bone filler material. The device further includes a delivery cannula in fluid communication with the membrane for providing bone filler material to the expandable membrane. The device also includes an evacuation cannula in fluid communication with the membrane for receiving a portion of the provided bone filler material from the membrane.

Another aspect of the present disclosure is directed to a method of augmenting void in a patient's bone, e.g., a void in a vertebral body. The method may include placing an expandable membrane into an interior void in a vertebral body and providing bone filler material to through a delivery cannula to the membrane. The membrane may be expanded by injection of an amount of bone filler material and a portion of the bone filler material may be removed from the membrane via an evacuation cannula.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

FIG. 5 is a partial cross-section of an example delivery cannula;

FIG. 6A is a partial side view of an example apparatus;

FIG. 6B is a partial side view of an example apparatus;

Like reference symbols in the various drawings indicate like elements.

DETAILED DESCRIPTION

Figure 1:
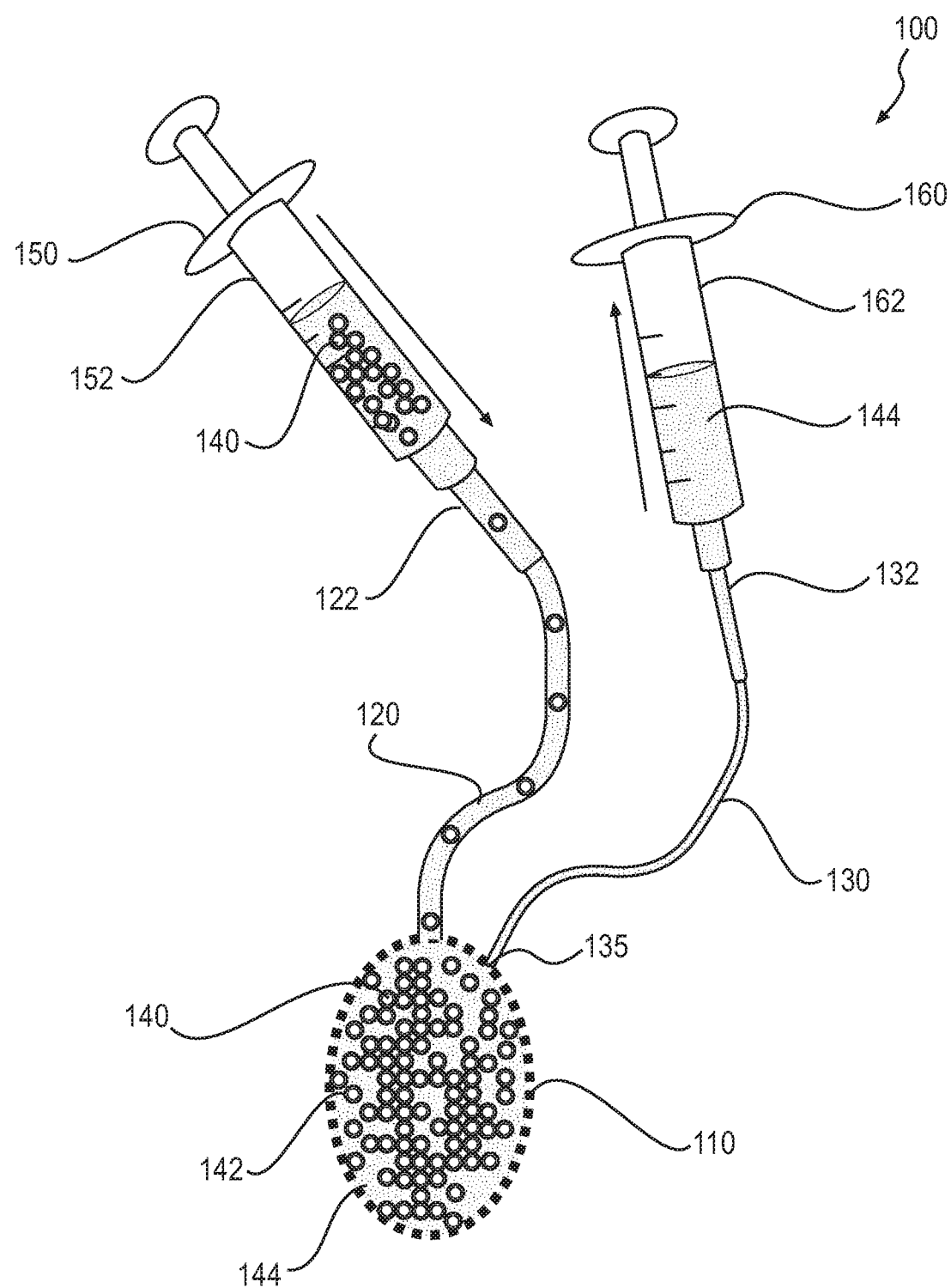
FIG. 1 is a plan view of an example apparatus.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The terminology includes the above-listed words, derivatives thereof, and words of similar import.

In addition, various components may be described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting.

Certain examples of the invention will now be described with reference to the drawings. In general, such embodiments relate to a porous or permeable membrane inserted into an interior volume/void in a targeted vertebral body and providing bone filler material to the device to restore the anatomy of the targeted vertebral body.

FIG. 1 provides a perspective view of an example apparatus 100. The apparatus 100 can include a membrane 110, delivery cannula 120 and evacuation cannula 130. The membrane 110 may be sized and configured for insertion into and location in a cavity/void/volume within a patient's bone (e.g., a targeted vertebral body V) or a void between bony parts (e.g., a targeted intervertebral disc space V). As will be provided in more detail below, the membrane 110 may be composed of a flexible, semi-flexible, or rigid material. The membrane 110 can be composed of a biocompatible material. For example the membrane 110 may be composed of a shape memory alloy (nitinol), titanium, stainless steel, metal alloy, resorbable material (e.g., resorbable polymer), non-resorbable material (e.g., non-resorbable polymer), ceramic, combination thereof. The membrane 110 can include an interior cavity for receiving bone filler material 140. The bone filler material 140 can include both solid material particles 142 and a carrier fluid 144 (e.g., saline). In an example apparatus 100, large solid material particles 142 can be broken into a granulate form and mixed with the carrier fluid 144 to create a granulate/fluid emulsion. The solid material 142 can include, for example, bone chips, autograft, allograft, or xenograft bone or any other filling material now or hereafter known in the art. Preferably the bone filler material 140 is a biocompatible bone cement capable of integrating with the surrounding bone tissue found in the bone cavity of the targeted intervertebral disc space V or vertebral body V. The bone filler material 140 may also include a radio-opaque material. Likewise, the bone filler material 140 can include a radiolucent material to enhance visibility of the bone filler material 140 and membrane 110 during radiographic imaging. It is contemplated that the filler material 140 can be tracked/imaged during the medical procedure placing the membrane 110 and filler material 140 into the void, i.e., intraoperative tracking. Likewise, it is contemplated that the injected and/or hardened filler material 140 can be imaged post-procedure.

Filling of the cavity formed in the vertebral body V (or intervertebral disc space V) and the stabilization of the targeted vertebral body V is accomplished by the injection of the bone filler material 140, the expansion of the membrane 110, and removal of all or a portion of the carrier fluid 144 such that the solid material 142 accumulates in the membrane 110, as will be described in greater detail below. The membrane 110 can remain in the void or can be removed to leave only the bone filler material 140. It is also contemplated that the expansion of the membrane 110 will include the controlled secretion of the bone filler material 140 out of or through the pores provided in the membrane 110.

The membrane 110 can be composed of a flexible material such that the membrane 110 expands when filled with the bone filler material 140. For example, the membrane 110 can be expanded from a first, non-expanded, configuration to a second, expanded, configuration via injection of the bone filler material 140 into the membrane 110. In the first, non-expanded, configuration, the membrane 110 can be sized and configured for insertion into interior cavity through a minimally invasive apparatus, e.g., a cannula. The membrane 110 can be flexible such that the shape of the second, expanded, configuration of the membrane 110 can be defined by the shape/volume of the bone cavity. In another example, the membrane 110 can be semi-constrained or selectively reinforced such that the second, expanded, configuration of the membrane 110 can be pre-defined. For example, the expanded configuration of the membrane 110 can define a sphere, a cylinder, a cone, a square, a rectangle, a torus, a dog bone, a regular shape, an irregular shape, or any other desired shape. In a further example, the expanded configuration of the membrane 110 can include a partially defined shape. That is, the expanded membrane 110 can define a predetermined shape and also be flexible and/or deformable based on the shape/volume defined by the bone cavity. In another example, the membrane 110 can be constructed from a shape memory material such that the membrane 110 has a first, flexible, configuration prior to insertion and a second, previously defined, shape after insertion.

Figure 2:
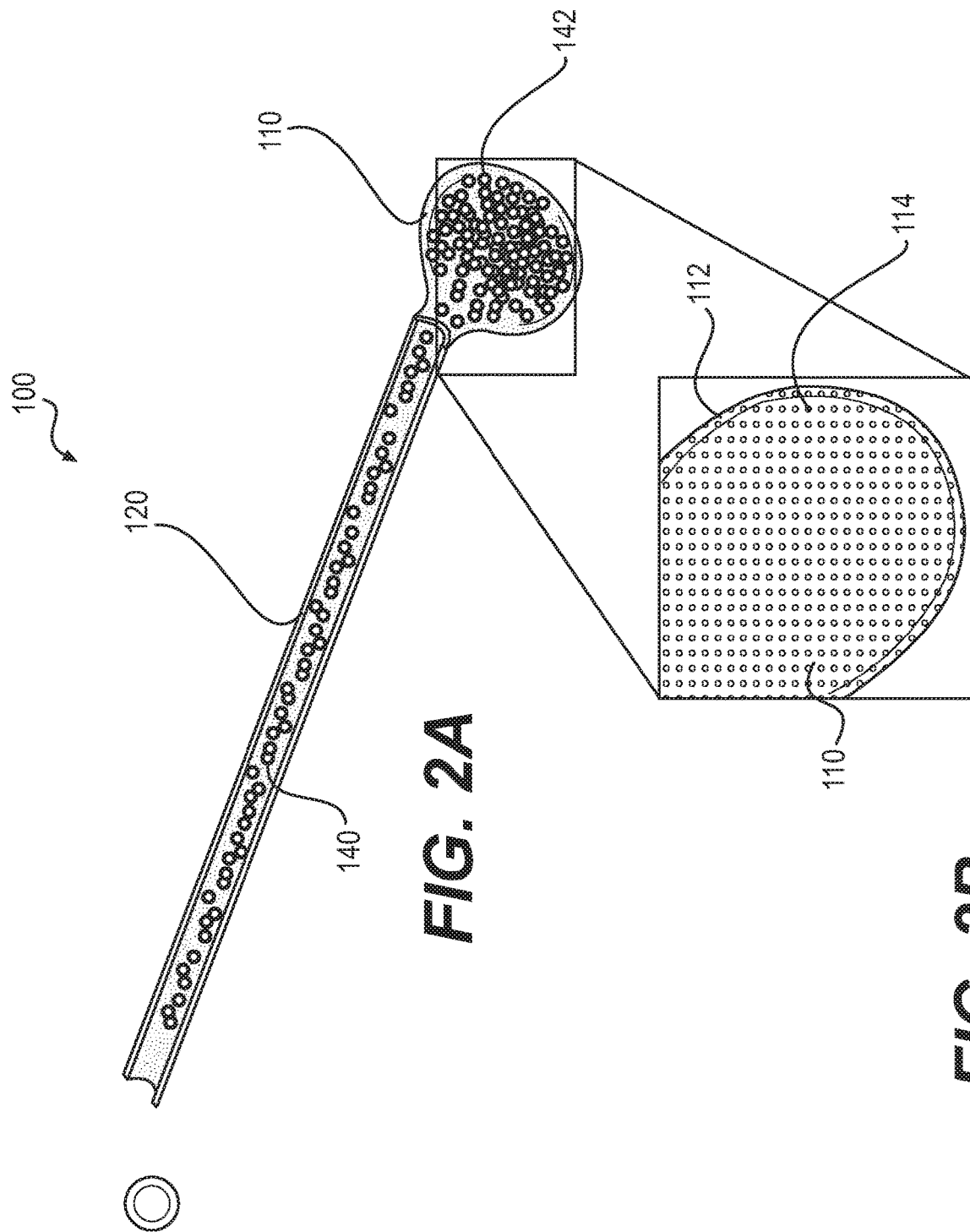
FIG. 2A is a partial cross-section view of an example apparatus.
FIG. 2B is a partial cross-section view of an example membrane.
Figure 3:
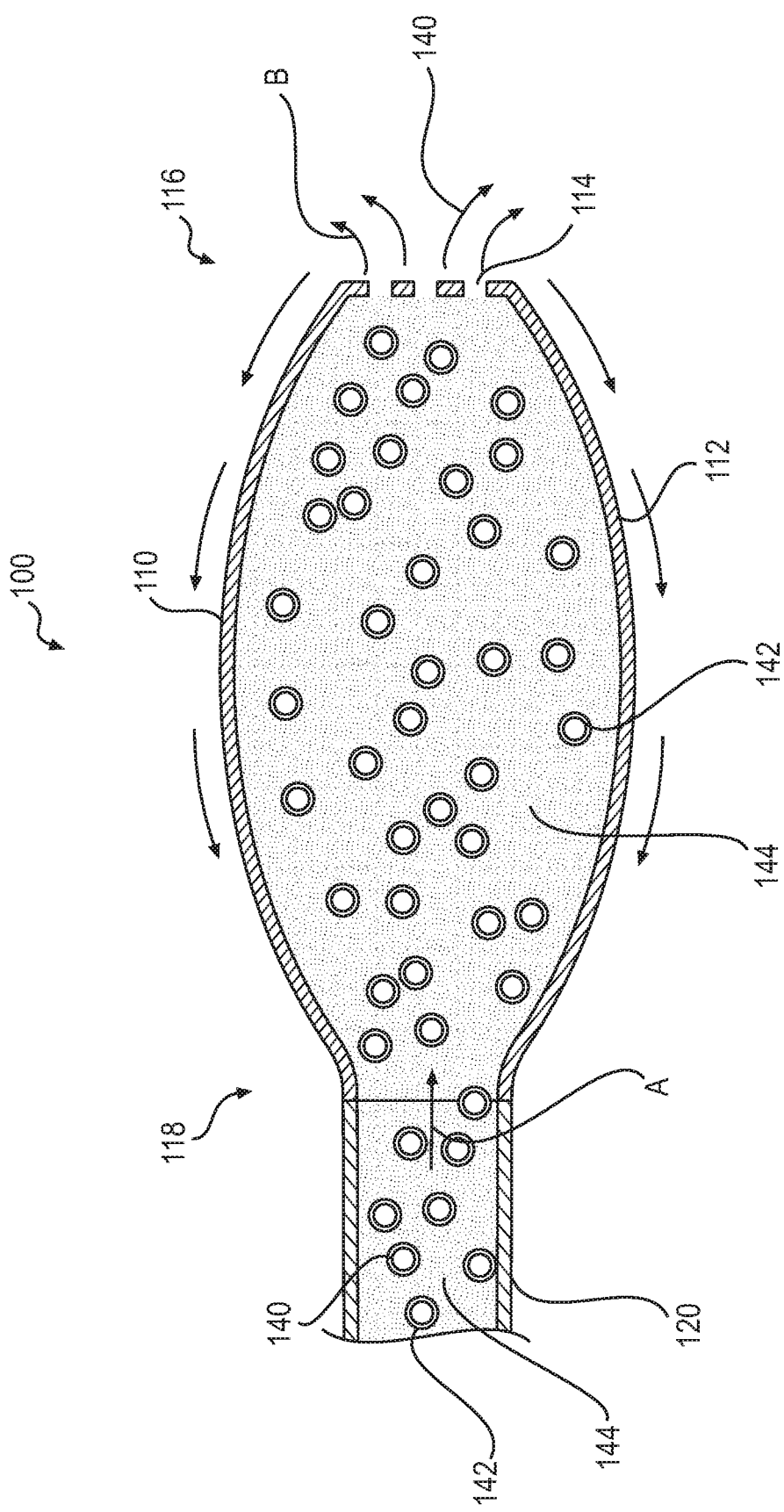
FIG. 3 is a partial cross-section view of an example apparatus.

FIG. 2A provides a partial cross-section view of an example apparatus 100 illustrating the delivery cannula 120 and a permeable membrane 110. FIG. 2B provides a partial cross-section view of an example membrane 110. As illustrated in FIG. 2B, the membrane 110 can include a body portion 112 constructed from a porous material. For example, the body portion 112 of the membrane 110 can include a plurality of pores/openings 114 allowing a portion of the bone filler material 140 (e.g., solid material 142 and/or carrier fluid 144) injected into the membrane 110 to flow out of or through the membrane 110 into the bone cavity. It is contemplated that the pores/openings 114 can be uniform in size and shape and be uniformly distributed on the body portion 112 of the membrane 110. That is, the pores/openings 114 can be located on the body portion 112 such that the outflow of filler material 140 is uniformly directed within the bone cavity. In another example, the openings 114 can be distinct in size, shape, and/or distribution on the body portion 112 of the membrane 110 such that outflow of the filler material 140 is directed to a desired location at a desired volume/velocity within the bone cavity. The pores/openings 114 can define a round, square, rectangular, oval, or any other regular or irregular shape. It is contemplated that the size, location, and number of the pores/openings 114 can be adjusted to provide for a controlled/directed secretion of filler material 140 from the membrane 110. For example, FIG. 3 provides a partial cross-section view of an example apparatus 100 including a membrane 110 having a porous section (pores/openings 114) located at the distal end 116 of the body portion 112. Accordingly, bone filler material 140 is provided via the delivery cannula 120 into the membrane 110 in the direction of arrow A. The carrier fluid 144 and solid material 142 (of a particular size) of the filler material 140 are excreted from the distal end 116 of the membrane 110 and into the bone cavity in the direction of arrows B. The bone filler material 140 secreted from the membrane 110 can form a filler material/cement layer around the membrane 110 to facilitate integration of the membrane 110 with the surrounding bone tissue. Accordingly, filing of the bone cavity and stabilization of the targeted vertebral body V is accomplished by the injection of the bone filler material 140, the expansion of the membrane 110, and the controlled secretion of the bone filler material 140 out of or through pores/openings 114.

As illustrated in FIG. 1, the apparatus 100 includes delivery cannula 120 and evacuation cannula 130. The delivery cannula 120 and the evacuation cannula 130 can be constructed from a flexible, semi-flexible, or rigid material. For example, the delivery cannula 120 and the evacuation cannula 130 can be constructed from a flexible biocompatible material such as a flexible polymer. In other examples, the delivery cannula 120 and/or evacuation cannula 130 can be constructed from medical grade silicone, PCU (poly carbonate urethane), PE (polyethylene), or a super-elastic shape memory alloy, etc. In another example, the delivery cannula 120 and/or evacuation cannula 130 can be constructed from a flexible or rigid material that is woven, knitted, braided, or otherwise interlaced to form a flexible cannula. Because the delivery and evacuation cannulae 120, 130 can be flexible, the delivery and evacuation cannulae 120, 130 provide access to areas in the patient's spine inaccessible by rigid systems and can limit damage to body structures (muscle tissue, nerve structures, etc.) caused by delivery and use of more rigid cannulae. A flexible delivery cannula 120 and/or evacuation cannula 130 can be inserted into the target location in the patient's body using a steerable delivery cannula such that damage to internal body structures is avoided/limited. In an other example, a flexible delivery cannula 120 and/or evacuation cannula 130 can include a steerable structure such that the delivery cannula 120 and/or evacuation cannula 130 is itself guidable to the desired location within the patient. The location of the delivery cannula 120 and/or evacuation cannula 130 can be monitored and tracked using various navigation and/or neuromonitoring tools known in the art.

The delivery cannula 120 is in communication with the membrane 110 and is sized and configured to provide bone filler material 140 (carrier fluid 144 and/or solid material 142) to the expandable membrane 110. The delivery cannula 120 can be sized to deliver both the solid material 142 and the carrier fluid 144 of the bone filler material 140 to the membrane 110. The evacuation cannula 130 is also in fluid communication with the membrane 110 and is sized and configured to receive a portion of the bone filler material 140 provided to the membrane 110 by the delivery cannula 120. The evacuation cannula 130 can be sized to receive the carrier fluid 144 and/or solid material 142 particles of a predetermined size. The evacuation cannula 130 can be used to remove bone filler material 140 (carrier fluid 144 and/or solid material 142) from the membrane 110 during and/or after expansion of the membrane 110 within the bone cavity. For example, bone filler material 140 may be removed during expansion in an effort to maintain a desired pressure and/or desired expansion of the membrane 110. Bone filler material 140 may also be removed from the membrane 110 after expansion. For example, all or a portion of the carrier fluid 144 may be removed from the membrane 110 such that the solid material 142 of the bone filler material 140 accumulates in the membrane 110. In an other example, carrier fluid 144 along with solid material 142 of a particular size may be removed via the evacuation cannula 130 such that solid material 142 of an other size remains in the membrane 110.

It is contemplated that the delivery cannula 120 and the evacuation cannula 130 are releasably coupled to the membrane 110 such that once the desired amount of bone filler material 140 has been delivered to the membrane 110 and the expanded membrane 110 is at its desired configuration, the delivery cannula 120 and the evacuation cannula 130 can be removed/released from the membrane 110 and the membrane 110 can remain as an implant in the cavity.

To facilitate delivery bone filler material 140 to the membrane 110, the apparatus 100 can include an input member 150. As illustrated in FIG. 1, the proximal end 122 of the delivery cannula 120 can be coupled to and in fluid communication with the input member 150. The input member 150 can direct bone filler material 140 into the delivery cannula 120 and thereby into the membrane 110. The input member 150 can direct bone filler material 140 at a predetermined rate and pressure. An example input member 150 includes a syringe. The input member 150 can include a storage element 152 for storing a quantity of bone filler material 140 for insertion into the membrane 110. The input member 150 can be used to adjust the proportion/ratio of the solid material 142 to the carrier fluid 144 in the bone filler material 140 delivered to the membrane 110.

To facilitate removal of bone filler material 140 from the membrane 110, the apparatus 100 can include an output member 160. As illustrated in FIG. 1, the proximal end 132 of the evacuation cannula 130 can be coupled to and in fluid communication with the output member 160. The output member 160 can direct bone filler material 140 through the evacuation cannula 130 and away from the membrane 110. The output member 160 can include a storage element 162 for storing a quantity of bone filler material 140 received from the membrane 110. In an example apparatus 110, the output member 160 can be operably coupled to a suction device for drawing the portion of the bone filler material 140 through the evacuation cannula 130 and away from the membrane 110. The output member 160 can direct bone filler material 140 from the membrane 110 at the same rate and/or pressure as the input member 150 delivers bone filler material 140. In another example, the output member 160 can direct bone filler material 140 from the membrane 110 at a different and/or varying rate and/or pressure than the input member 150 delivers the material to the membrane 110. In an example apparatus 100, the rate and/or pressure (suction) of the output device 160 is determined by the suction device the output device 160 is coupled to. In a further example apparatus 100, the particle size and rate of removal from the membrane 110 can be defined based on the size/area of the coupling between the membrane 110 and the evacuation cannula 130. For example, the evacuation cannula 130 having a circular cross-section can have a radial cross-section defining an area (e.g., $A=\pi r^2_{evacuation}$) less than the area of the radial cross section of the delivery cannula 120 having a circular cross-section (e.g., $A=\pi r^2_{delivery}$). As such, the evacuation cannula 130 may withdraw filler material 140 from the membrane 110 at a rate and volume less than that of the delivery cannula 120. Similarly, the area defining the coupling between the evacuation cannula 130 and the membrane 110 can define the size of particles that may be transmitted into the evacuation cannula 130. For example, the area defined by the coupling may be such that the evacuation cannula 130 may only receive carrier fluid 144 and solid material 142 of a particular size. In another example, a filter 135 can be coupled to the evacuation cannula 130 at a location between the evacuation cannula 130 and the membrane 110 such that the filter 135 prevents bone filler material 140 of a predetermined size from passing into the evacuation cannula 130. In an example apparatus 100, the composition of the removed bone filler material 140 can comprise at least 50% carrier fluid 144. In a further example, the composition of the removed bone filler material 140 can comprise greater than 50% carrier fluid 144.

As illustrated in the example apparatus 100 of FIG. 1, the delivery cannula 120 and the evacuation cannula 130 can be coupled to the membrane 110 at different locations. For example, the delivery cannula 120 can be located adjacent to the evacuation cannula 130. In an other example (not shown), the evacuation cannula 130 can be located at a location distant or opposite on the membrane 110 from the delivery cannula 120. For example, the delivery cannula 120 can be located on the proximal end 118 of the membrane 110 and the evacuation cannula 130 can be located at the distal end 116 of the membrane 110. It is contemplated that the evacuation cannula 130 and the delivery cannula 120 can be located at any position on the membrane 110.

Figure 4:
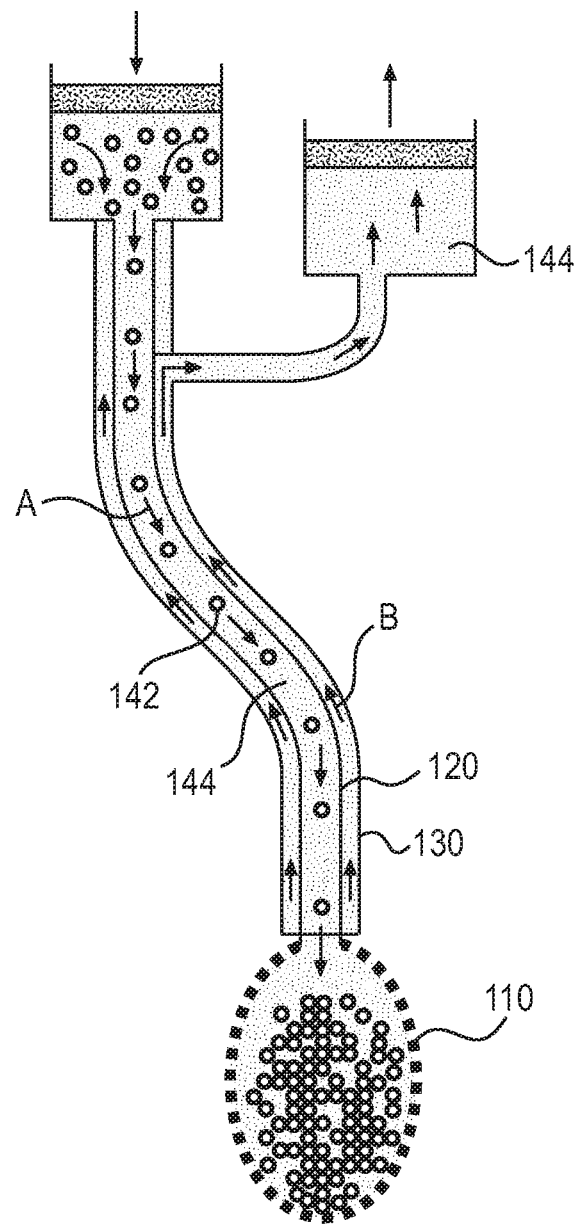
FIG. 4 is a plan view of another example apparatus.

In another example apparatus 100 illustrated in FIG. 4, the delivery cannula 120 extends within the evacuation cannula 130. FIG. 4 provides a plan view of the example apparatus 100 having the combined delivery/evacuation cannula design. FIG. 5 provides a partial cross-section view of the example delivery cannula 120 and evacuation cannula 130. As illustrated, the delivery cannula 120 extends through the evacuation cannula 130 providing filling material 140 to the membrane 110 in the direction of arrows A. As outlined above, the evacuation cannula 130 can be used to remove carrier fluid 144 and solid material 142 of a particular size from the membrane 110. As illustrated in FIGS. 4 and 5, the evacuation cannula 130 can terminate proximate the membrane 110. For example, the evacuation cannula 130 can remove carrier fluid 144 (and/or solid material 142) that passes through the openings 114 provided in the membrane 110. In another example (not shown), the evacuation cannula 130 can be coupled to the membrane 110 such that carrier fluid 144 (and/or solid material 142) can be removed directly from the main cavity of the membrane 110. The evacuation cannula 130 removes the carrier fluid 144 and the particular size solid material 142 in the direction of arrows B. The particle size and rate of removal from the membrane 110 can be defined based on the size/area of the coupling between the membrane 110 and the evacuation cannula 130. Accordingly, the coupling area of the evacuation cannula 130 and the membrane 110 is calculated based on the area defined by difference between the evacuation cannula 130 and the delivery cannula 120 (e.g., assuming the evacuation cannula 130 and delivery cannula 120 have circular cross-sections, the evacuation cannula 130 coupling area Area= $\pi(r_{evacuation})^2-\pi(r_{delivery})^2$). As such, the evacuation cannula 130 can be configured to receive carrier fluid 144 and solid material 142 of a particular size. As illustrated in FIG. 5, element "d" identifies the difference between the radius of the delivery cannula 120 and the radius of the evacuation cannula 130. Accordingly, this difference (d) identifies the largest particle size of the solid material 142 capable of being withdrawn via the evacuation cannula 130. It is also contemplated that the difference (d) between the delivery cannula 120 and the evacuation cannula 130 can be such that only the carrier fluid is removed from the membrane 110. For example, the difference (d) can be such smaller than the particle size of the solid material 142 included in the filler material 140.

In a further example, the membrane 110 can be constructed from a flexible material and include a withdraw element 170 capable of withdrawing the flexible membrane 110 off the filler material 140. FIGS. 6A and 6B provide side views of an example membrane 110 constructed from a flexible material and including a withdraw element 170 for removing the membrane 110 material from the filler material 140. The withdraw element 170 can be coupled to the membrane 110 to permit the membrane 110 to release from the filler material 140 upon movement of the withdraw element 170 towards the proximal end 118 of the membrane 110. An example withdraw element 170 can include a flexible wire/string. Another example withdraw element 170 can include a tube coupled to the membrane 110. As illustrated in FIG. 6A, with withdraw element 170 can be coupled to the distal end 116 of the membrane 110 at point A and withdrawn in a direction towards the proximal end 118 of the membrane 110 illustrated by arrows B. FIG. 6B illustrates the material of the flexible membrane 110 partially withdrawn off the filler material 140 and folded back onto the remaining membrane 110 material, area C. As in this example, because the membrane 110 does not remain in the patient, it can be considered as part of the apparatus 100 facilitating delivery and placement of the biomaterial in the cavity.

In another example (now shown), the withdraw element 170 is coupled to the membrane 110 such that as the withdraw element 170 is moved is a direction towards the proximal end 118, the membrane 100 is removed from the filler material 140 without folding back onto itself. For example, the withdraw element 170 can be coupled to the proximal end 118 of the membrane 110 and/or along the length of the membrane 110. Movement of the withdraw element 170 causes the membrane 110 to release from the delivery cannula 120 and move over the filler material 140 and the delivery cannula 120 in a direction towards the proximal end 118 of the apparatus 100.

In operation, the bone filler material 140 can be provided to the membrane 110 via the delivery cannula 120. The carrier fluid 144 (and possibly some solid material 142 depending in contact area defined by the evacuation cannula 130) is removed from the membrane 110. Once the filler material 140 is sufficiently set/formed within the bone cavity, the withdraw element 170 can be used to drawn the flexible material of the membrane 110 off the set filler material leaving only the filler material within bone cavity.

Figure 6C:
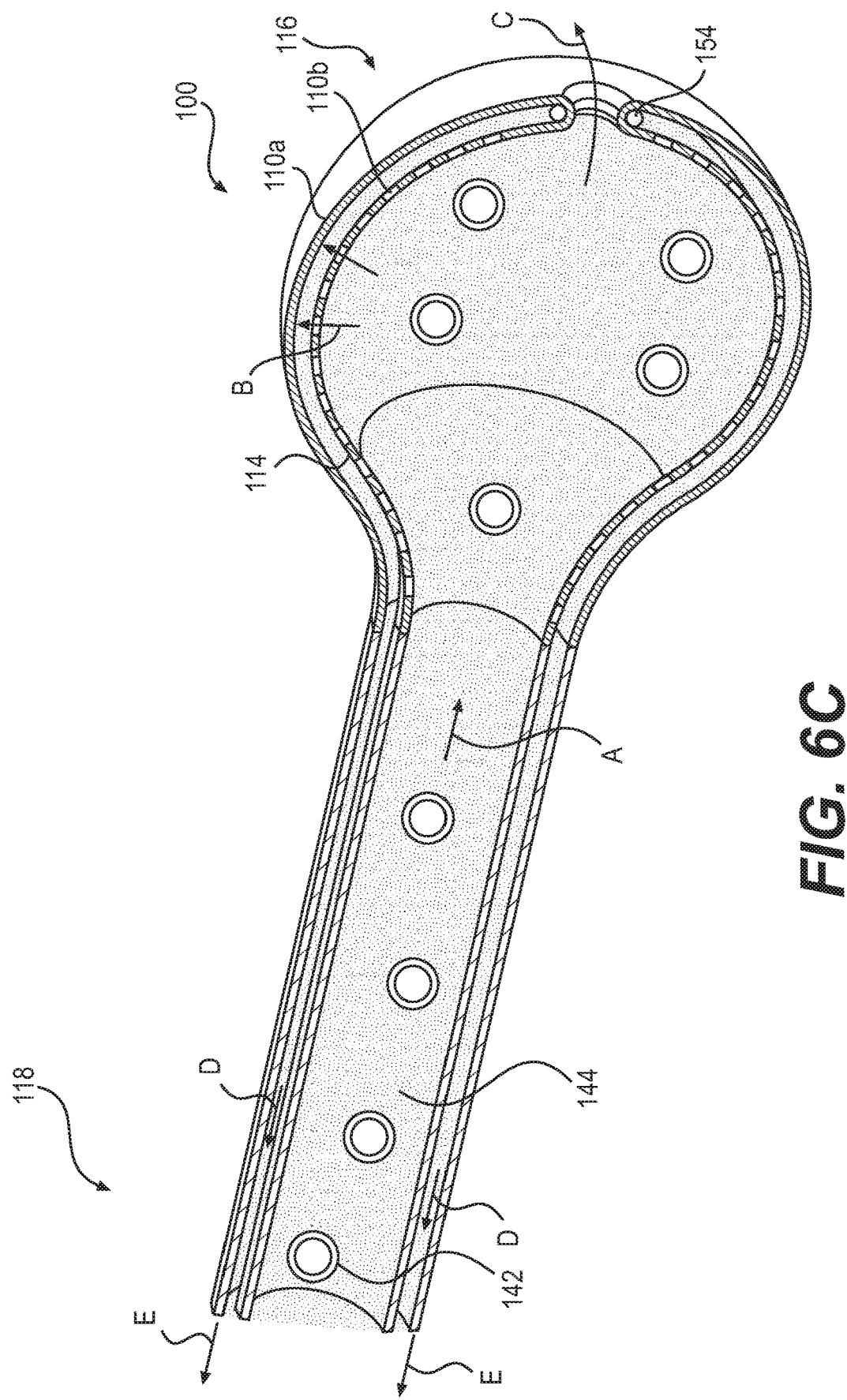
FIG. 6C is a partial side view of an example apparatus.

FIG. 6C provides a perspective cross-section view of another example membrane 110. The membrane 110 can be constructed from a flexible material and include an outer layer 110a and an inner layer 110b. The outer layer 110a can be coupled to the evacuation cannula 130/outer cannula of the apparatus 100. The inner layer 110b can be coupled to the delivery cannula 120/inner cannula of the apparatus 110. Either one of the outer layer 110a or the inner layer 110b can alternatively be permeable. For example, as illustrated in FIG. 6C, the inner layer 110b can include openings 114 and the outer layer 110a can be solid. It is also contemplated that both the outer layer 110a and the inner layer 110b can be permeable, including openings 114 (of similar or varying size) to provide for the flow of carrier fluid 144 and/or solid material 142, or impermeable. The membrane 110 can include a ring 154 located at the distal end 116 of the membrane 110. The ring 154 can provide a coupling point for the outer layer 110a and inner layer 110b. The ring 154 can include an opening between the inner volume of the membrane 110 and the void within the patient. The opening in the ring 154 can be sized to permit the flow of carrier fluid 144 and/or solid material 142 of a particular size from the inner volume of the membrane to the void. In another example (not shown), the ring can no include an opening.

In operation, bone filler material 140 is provided to the membrane 110 via the delivery cannula 120 in the direction of arrow A. Solid material 142 will collect within the interior volume defined by the inner layer 110b. The carrier fluid 144 (and possibly some solid material 142 depending on the area defined by the openings in the inner and/or outer layers 110b, 110a and/or the opening in the ring 154) is removed from the membrane 110. For example, where the inner layer 110b and/or outer layer 110a are permeable, the carrier fluid 144 and/or solid material 142 (of a particular size) can pass from the inner volume of the membrane 110 to the evacuation cannula 130, in the direction of arrows B. It is also contemplated that carrier fluid 144 and/or solid material 142 (of a particular size) can pass through the opening in the ring 154 and into the void in the direction of arrow C. Where the outer layer 110a is permeable, carrier fluid 144 and/or solid material 142 that has passed through the opening in the ring 154 can also pass into the evacuation cannula 130 via the openings 114 in the outer layer 110a. The carrier fluid 144 and/or solid material 142 is then drawn through the evacuation cannula 130 in the direction of arrows D. Once the filler material 140 is sufficiently set/formed within the inner volume of the membrane 110, the membrane 110 can be removed from the set filler material, leaving the filler material 140 within the cavity. The evacuation cannula 130/outer cannula of the apparatus 100 can facilitate removal of the membrane 110 from the filler material. For example, as evacuation cannula 130/outer cannula of the apparatus 100 can be moved with respect to the delivery cannula 120/inner cannula of the apparatus 110, the outer layer 110a is moved with respect to the inner layer 110b. In an example apparatus 100, as the evacuation cannula 130 is moved in the direction of arrows E, away from the membrane 100, the outer layer 110a (and membrane 110) is removed from the filler material 140. The ring 154 can be made of a fragile material that such that it will fracture when sufficient force is applied from the outer layer 110a/evacuation cannula 130. Once the ring 154 is fractured, the membrane 100 (inner layer 110b and outer layer 110a) can be withdrawn off of the filler material. Once removed from the filler material 140, the inner layer 110a can separate from the delivery cannula 120 and the entirety of the membrane 110 removed from the filler material 140, leaving only the filler material 140 within the cavity. In another example, the ring 154 can be constructed from a flexible material such that the ring 154 stretches/flexes as the membrane 110 is removed from the filler material 140.

Figure 7:
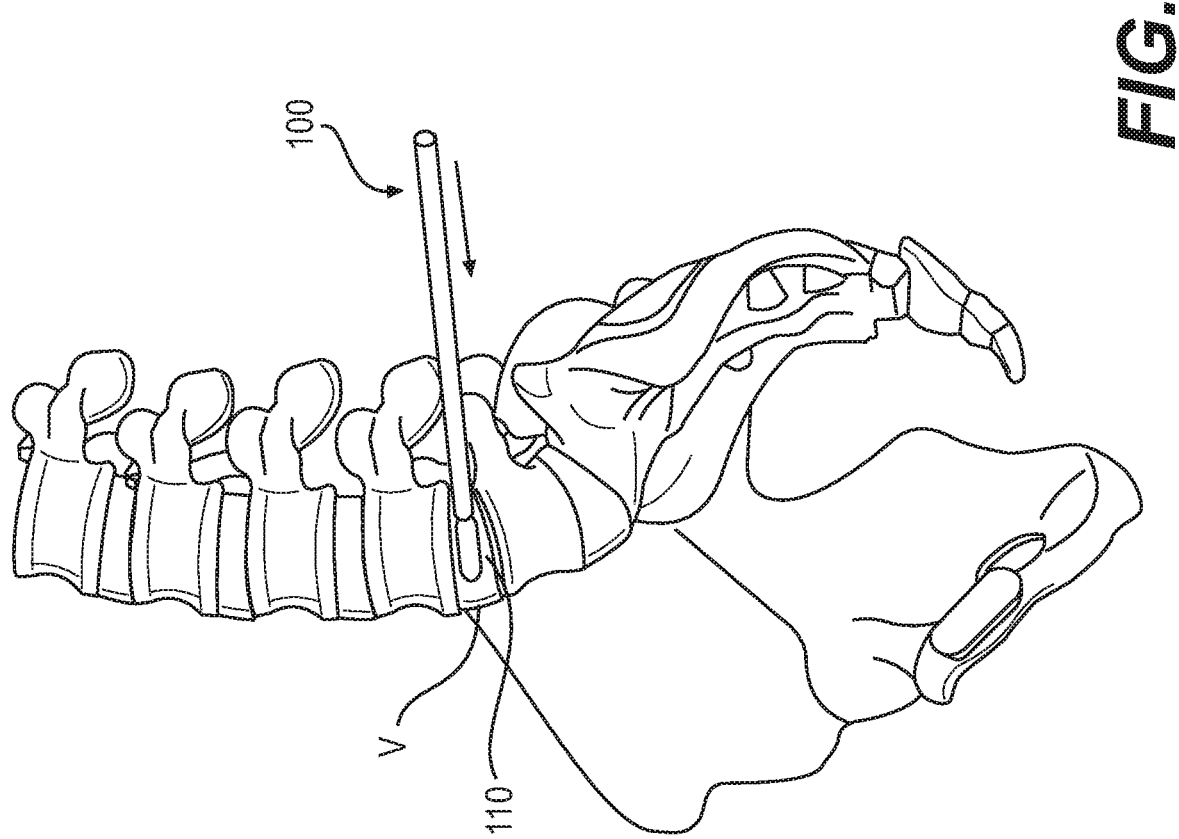
FIG. 7 is a partial view of an example intervertebral disc space during insertion and expansion of the membrane.

In use, the membrane 110, in its first, non-expanded, configuration is inserted preferably via a minimally invasively apparatus (e.g., cannula) into a targeted zone. FIG. 7 provides a partial view of an example target zone including an intervertebral disc space V during insertion and expansion of the membrane 110. Bone filler material 140 is then provided to the membrane 110 through the delivery cannula 120 by input member 150. The membrane 110 is expanded from an insertion configuration to an expanded configuration via injection of the bone filler material 140 into the inner cavity of the membrane 110. Expansion of the membrane 110 can compress and/or contact the surrounding cancellous bone tissue of the targeted intervertebral disc space V thereby forming and/or filling the cavity. The membrane 110 can expand to define a predetermined or predisposed shape. In another example, the shape of the expanded membrane 110 can be defined by the shape of the bone cavity. Expansion of the membrane 110 can reposition and stabilize the surrounding bone and/or bone tissue. That is, the membrane 110, in the expanded configuration, is structurally strong enough to impart a force to the surrounding bone tissue in the cavity of the targeted intervertebral disc space V sufficient to restore the anatomical alignment of the intervertebral disc space V until hardening of the injected bone filler material is complete.

Figure 8:
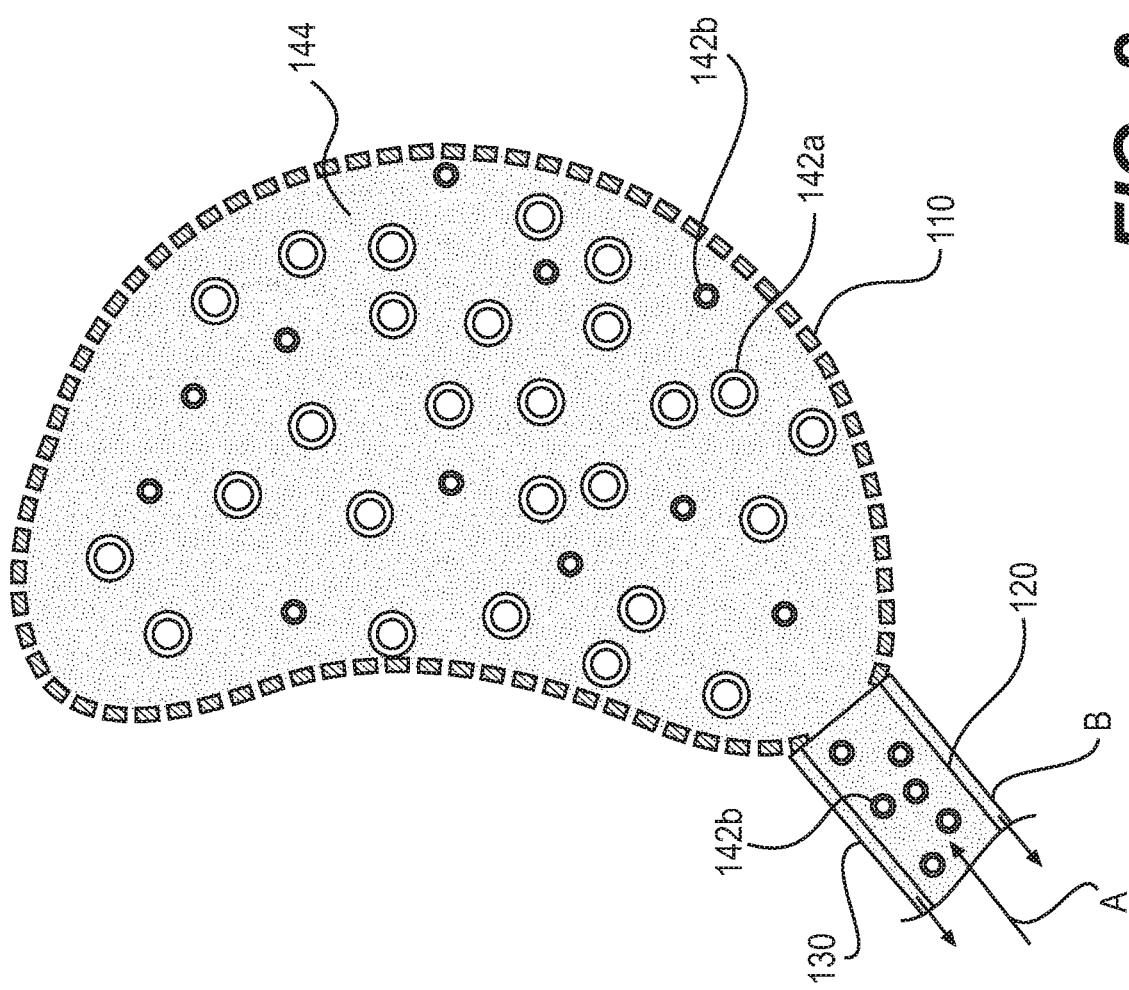
FIG. 8 is a partial cross-section view of an example apparatus.

FIG. 8 provides a partial cross-section view of an example membrane 110 during injection of the bone filler material 140 in the direction for arrow A. In an example apparatus 100, solid material 142 of constant (or varying) size is distributed throughout the bone filler material 140 and injected into the membrane 110. In another example apparatus 100, the bone filler material 140 is injected into the membrane 110 by injecting a first volume of bone filler material 140 having a first solid particle size 142a and subsequently injecting a second volume of bone filler material 140 having a second solid particle size 142b such that the first particle size 142a is greater than the second particle size 142b. That is, the composition of the bone filler material 140 is adjusted such that filler material 140 having a large particle size (e.g., first solid particle 142a) is injected first into the membrane 110 and filler material 140 having a smaller particle size (e.g., second solid particle 142b) is injected second into the membrane 110. It is further contemplated that filler material 140 with solid particles having a smaller particle size may be injected first into the membrane 110 followed by filler material 140 with solid particles having a larger particle size.

A portion of the bone filler material 140 (e.g., the carrier fluid 144 and/or solid material 142 of a particular size) may be removed from the membrane 110 through the evacuation cannula 130 (direction of arrow B in FIG. 8) by the output member 160. The bone filler material 140 may be removed from the membrane 110 until a desired proportion of solid material 142 to carrying fluid 144 is present in the filler material 140 inserted into the membrane 110. It is also contemplated that the filler material 140 may be injected into and removed from the membrane 110 until the desired portion of solid material 142 is present in the membrane 110.

The outer surface of the membrane 110 can be porous such that an amount of bone filler material 140 is secreted out of or through the membrane 110. In another example, the pores/openings 114 can be located on the body portion 112 of the membrane 110 such that the bone filler material 140 is directionally secreted from the membrane 110. In an example apparatus, a relatively small amount of bone filler material 140 may be secreted out of or through the membrane 110 via one or more pores/openings 114 formed in the membrane 110. Once secreted, the bone filler material 140 can cure to form a cement layer around the membrane 110 that integrates with the surrounding bone tissue.

Figure 9:
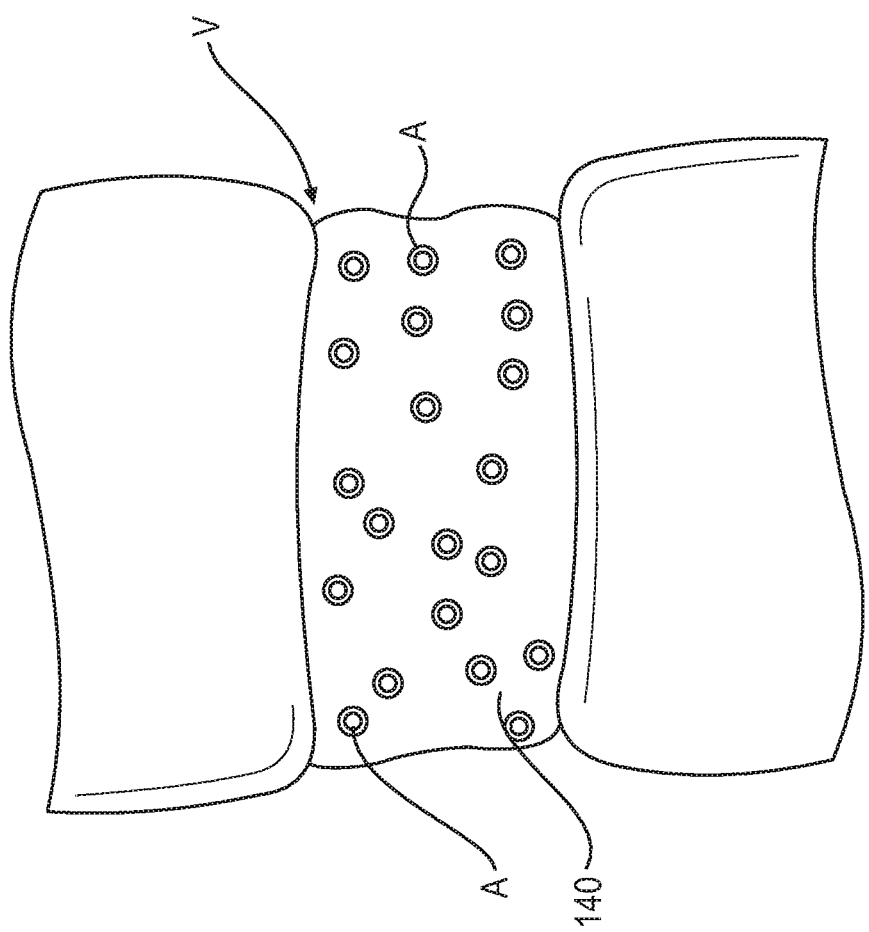
FIG. 9 is a partial cross-section view of an example apparatus within the intervertebral disc space.

As outlined above, the bone filler material 140 can include a radiolucent material to enhance visibility of the membrane 110 during radiographic imaging. Accordingly, radiographic (x-ray) imaging may be used during expansion of the membrane 110 to determine the desired distribution of filler material 140. Likewise, radiographic (x-ray) imaging may be used during injection of filler material 140 to determine the desired repositioning of the intervertebral disc space V and expansion of the membrane 110. FIG. 9 provides an example radiographic image illustrating radiolucent material (elements A) present in the filler material 140.

Once the bone filler material 140 is inserted into the membrane 110 (and the desired portion of carrying fluid 144 and/or solid material 142 has been removed), the bone filler material 140 begins to cure within the bone cavity. In an example apparatus, the membrane 110, enclosing the cured bone filler material 140, remains within the bone cavity of the targeted vertebral body V/intervertebral disc space V and is considered part of the implanted material. This implant-type membrane 110 can assist in load bearing and structural support of the vertebral body V/intervertebral disc space V as the bone filler material 140 cures. In another example, the implant-type membrane 110 is constructed from a bioresorbable material that is absorbed, over time, into the body.

In a further example, the membrane 110 is constructed from a flexible material such that, as the bone filler material 140 cures within the cavity, the flexible material of the membrane 110 is removed from the cured (and/or partially cured) bone filler material 140, leaving the bone filler material 140 within the cavity. In such an example, the membrane 100 can be considered part of the apparatus 100 for facilitating delivery and placement of the bone filler material to the void.

As outlined above, the membrane 110, delivery cannula 120, and evacuation cannula 130 may be composed of a biocompatible material known including, for example, metals such as titanium, titanium alloys, stainless steel and cobalt chromium, cobalt chromium molybdenum (Co-CrMo), or other metals. Other materials include, for example, composites, polymers, or ceramics. In one example, one or more components of the apparatus 100 can be constructed from a radiopaque material including, for example, stainless steel such as 17-4PH stainless steel. Likewise, one or more components described herein can be constructed from a radiolucent material to enhance visibility of the assembly during radiographic imaging. Example radiolucent materials can include "life science" grade PEEK (Ketron 450G PEEK). Life science grade PEEK can improve wear and abrasion characteristics as well as provide high yield strength. A coating may be added or applied to the various components described herein to improve physical or chemical properties, such as a plasma-sprayed titanium coating or Hydroxypatite. Moreover, skilled artisans will also appreciate that the various components herein described can be constructed with any dimensions desirable for implantation and cavity creation.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. An apparatus for providing a bone filler material to a cavity in a patient's bone, the apparatus comprising:
   an expandable membrane sized and configured to be located within the cavity in the patient's bone, the expandable membrane having an interior volume for receiving the bone filler material;

a delivery cannula in fluid communication with the membrane for providing bone filler material to the membrane;

an evacuation cannula in fluid communication with the membrane for receiving a portion of the provided bone filler material from the membrane during and after expansion of the membrane within the cavity in the patient's bone, and a filter coupled to the evacuation cannula at a location between the evacuation cannula and the membrane such that the filter prevents bone filler material of a predetermined size from passing into the evacuation cannula.

2. The apparatus of claim 1, wherein the membrane is composed of a flexible material.

3. The apparatus of claim 2, wherein at least a portion of the delivery cannula and the evacuation cannula are constructed from a flexible material.

4. The apparatus of claim 1, wherein the membrane is porous and includes a plurality of openings allowing a portion of the bone filler material to flow out of the membrane and into the cavity in the patient's bone during expansion of the membrane.

5. The apparatus of claim 4, wherein the size, shape, or location of the plurality of openings allows for the controlled outflow of a portion of the bone filler materials.

6. The apparatus of claim 4, wherein the controlled outflow of the portion of bone filler material is directed to a desired location at a desired volume or velocity within the cavity in the patient's bone.

7. The apparatus of claim 1, wherein the membrane is composed of a biocompatible material including at least one of a shape memory alloy (nitinol), titanium, stainless steel, metal alloy, resorbable polymer, non-resorbable polymer, ceramic, combination thereof.

8. The apparatus of claim 1, wherein in the membrane is expandable from a first, non-expanded, configuration to a second, expanded, configuration via injection of the bone filler material into the membrane.

9. The apparatus of claim 8, wherein the membrane is configured such that the second configuration is capable of being defined by a shape of a cavity in a patient's bone.

10. The apparatus of claim 8, wherein the expandable membrane is sized and configured to accumulate solid material of the bone filer material within the interior volume of the expandable membrane such that the expandable membrane is maintained in the second, expanded, configuration.

11. The apparatus of claim 8, wherein the membrane includes a reinforcing member for restricting expansion of the membrane such that at least one of a size and a shape of the membrane in the second configuration is predefined.

12. The apparatus of claim 9, wherein the second configuration defines a shape including at least one of a sphere, a cylinder, a square, a rectangle, a cone, a torus, a dog bone, a regular shape, and an irregular shape.

13. The apparatus of claim 1, wherein the delivery cannula extends within at least a portion of the evacuation cannula.

14. The apparatus of claim 1, wherein the evacuation cannula is coupled to the membrane at a location other than a coupling location of the delivery cannula.

15. The apparatus of claim 1, further including an input member in fluid communication with the delivery cannula, the input member directing bone filler material into the delivery cannula.

16. The apparatus of claim 1, wherein the bone filler material includes a solid material and a carrying fluid, and the input member can adjust a ratio of the solid material to the carrying fluid in the bone filler material,
wherein the solid material comprises at least one of a biocompatible bone cement, bone chips, autograft, allograft, and xenograft bone.

17. The apparatus of claim 1, further including an output member in fluid communication with the evacuation cannula, the output member directing a portion of the bone filler material through the evacuation cannula away from the membrane.

18. The apparatus of claim 17, wherein the output member is operably coupled to a suction device for drawing the portion of the bone filler material through the evacuation cannula away from the membrane.

19. The apparatus of claim 1, wherein the evacuation cannula is configured to control the removal of the bone filler material from the expandable membrane during expansion to maintain at least one of a desired pressure and a desired expansion of the expandable membrane.

* * * * *